United States Patent [19]

Plessers

[11] 4,166,738
[45] Sep. 4, 1979

[54] METHOD FOR THE TREATMENT OF NODULAR OR VERMICULAR CAST IRON SAMPLES

[75] Inventor: Jacques J. Plessers, Houthalen, Belgium

[73] Assignee: Electro-Nite Co., Philadelphia, Pa.

[21] Appl. No.: 831,213

[22] Filed: Sep. 7, 1977

[30] Foreign Application Priority Data

Sep. 9, 1976 [FR] France .................................. 76 27172
Feb. 9, 1977 [FR] France .................................. 77 03557

[51] Int. Cl.² ............................................ C22C 33/08
[52] U.S. Cl. ..................................... 75/130 R; 75/129
[58] Field of Search .............................. 75/130 R, 129

[56] References Cited

U.S. PATENT DOCUMENTS

| | | | |
|---|---|---|---|
| 3,005,736 | 10/1961 | Peras | 75/130 R |
| 3,155,498 | 11/1964 | Jandras | 75/130 R |
| 3,210,183 | 10/1965 | Ototani | 75/130 R |
| 3,546,921 | 12/1970 | Bourke | 75/130 R |
| 3,663,212 | 5/1972 | Heine | 75/130 R |

*Primary Examiner*—P. D. Rosenberg
*Attorney, Agent, or Firm*—Seidel, Gonda, Goldhammer & Panitch

[57] ABSTRACT

A sample of nodular or vermicular cast iron has magnesium and/or cerium atoms therein neutralized by the addition of selenium or sulphur in the presence of tellurium.

8 Claims, 3 Drawing Figures

METHOD FOR THE TREATMENT OF NODULAR OR VERMICULAR CAST IRON SAMPLES

BACKGROUND

The present invention relates to a method for the promotion of white solidification of nodular or vermicular cast iron samples which is required for the determination of the carbon content and the carbon equivalent of such samples from the study of their duly recorded cooling curves. It is common practice to sample molten iron or steel for studying or controlling some properties of the molten metal.

It is already a common practice to determine some properties of molten iron from the study of the duly recorded cooling curves. This method is based upon the fact that there is a relation between the temperature corresponding to the liquidus arrest of an iron sample and its carbon equivalent. More recently, it has been determined that there is also a relation between the liquidus and metastable solidus temperatures and the carbon content of an casting (Foundry, Management and Technology, July 1974, pages 80 to 83). The eutectic austenitecementite temperature is generally called the solidus temperature.

The exact and clear detection of solidus and liquidus levels in a cooling curve of a hypereutectic iron sample requires that the the sample solidifies white. For this reason, the known method mentioned hereabove could until now only be applied to hypoeutectic and non-nodular and non-vermicular hypereutectic castings.

As far as the analysis of hypereutectic castings is concerned, it is already known (U.S. Pat. No. 3,546,921) to add to samples an element that is able to stabilize the carbide in order to delay the graphite formation. Such an element can be tellurium, bismuth, cerium, magnesium and the like, and is added in a quantity not surpassing 0.40% in weight of the sample.

The interaction of magnesium with tellurium when treating the casting was the object of a study published in the journal Russian Castings Production (1970, 3, pages 146–147) from which it appears that tellurium, even when added in small quantities to the casting, can have a denodularisation effect due to its combination with magnesium. On the other hand, the inhibitory effect of tellurium and of selenium, as well as of sulphur upon the formation of spheroidal graphite in castings has recently been described in the journal Imono (47, 1976, 12, 836). None of the above-mentioned studies however discloses how to obtain white solidification of a nodular or vermicular casting in a way which is easy and reliable.

It should be noted that not only the study of the cooling curve but also analysis with an emission-spectrometer requires the white solidification of a sample of such a molten iron.

The aim of the invention is to provide a solution to the problem relating to the obtainment of such a type of solidification.

SUMMARY OF THE INVENTION

According to the invention, a method of binding at least the majority of magnesium and cerium atoms present in the sample to be studied is disclosed in order to allow the known catalytic action or carbidic stabilizing properties of tellurium added to said sample to take effect.

For the purpose of illustrating the invention, there is shown in the drawings a form which is presently preferred; it being understood, however, that this invention is not limited to the precise arrangements and instrumentalities shown.

The method according to the invention consists in fixing the majority of magnesium and cerium atoms in a sample of molten iron which has been treated to produce a nodular or vermicular hypereutectic iron sample from the very beginning of the temperature measurement in order to allow the catalytic or carbide stabilizing action of tellurium added for this purpose to take place in the sample in order to avoid the formation of magnesium or cerium telluride.

According to the invention, this fixation of magnesium and cerium can be obtained by adding to the sample an excess of tellurium, selenium, or sulphur, considered individually or in mixtures, in the pure state or in compound form (especially when sulphur is concerned). It is apparent that one can choose compounds which are able to liberate one or more active elements as well. If one chooses tellurium as a fixing agent for magnesium or cerium and as catalyst, a quantity of more than 0.40% in weight of the sample has to be added. Indeed, nodular or vermicular castings generally contain up to 0.60% in weight of magnesium, which theoretically requires 0.32% in weight of tellurium for fixing the magnesium while a sufficient quantity of tellurium remains in order to perform the required catalytic or carbide stabilizing effect.

In practice, the yield of tellurium is only 75% at its best, thus, a quantity of tellurium of more than 0.40% in weight has to be used. When selenium is used as the fixing agent, the minimum quantity that has to be introduced into the sample crucible is 0.30% in weight in order to obtain sufficient yield, the theoretical minimum quantity being 0.20% in weight. For sulphur, the optimum quantity of pure sulphur to be introduced into the sample crucible ranges from 0.08 to 1.00% in weight. The quantities mentioned hereabove guarantee a sufficient fixation of the magnesium and cerium atoms in all common compositions of nodular or vermicular molten iron samples.

From the economical point of view, of the elements covered by the invention, sulphur has to be preferred. Selenium produces toxic gases and requires a pouring temperature in excess of 1350° C. Furthermore, the melting and boiling points of sulphur are considerably lower than those of tellurium and selenium and consequently it will diffuse much more quickly into the sample. It is obvious that when selenium and sulphur are used, the usual quantity of tellurium (about 0.1% in weight) also has to be introduced into the sample crucible to promote the desired white solidification.

Figure 2:
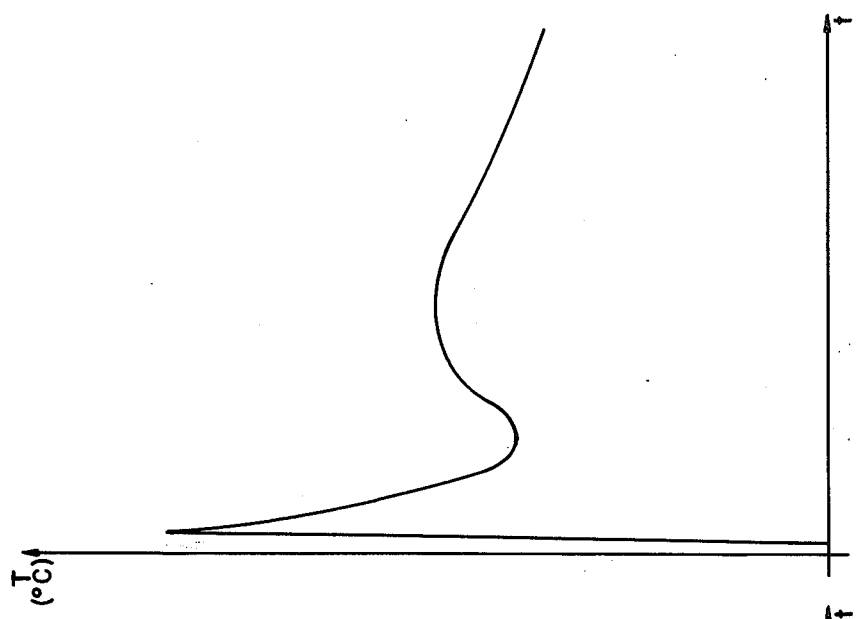
FIG. 2 shows a solidification curve of a sample of the same iron, obtained in the conventional way.
Figure 1:
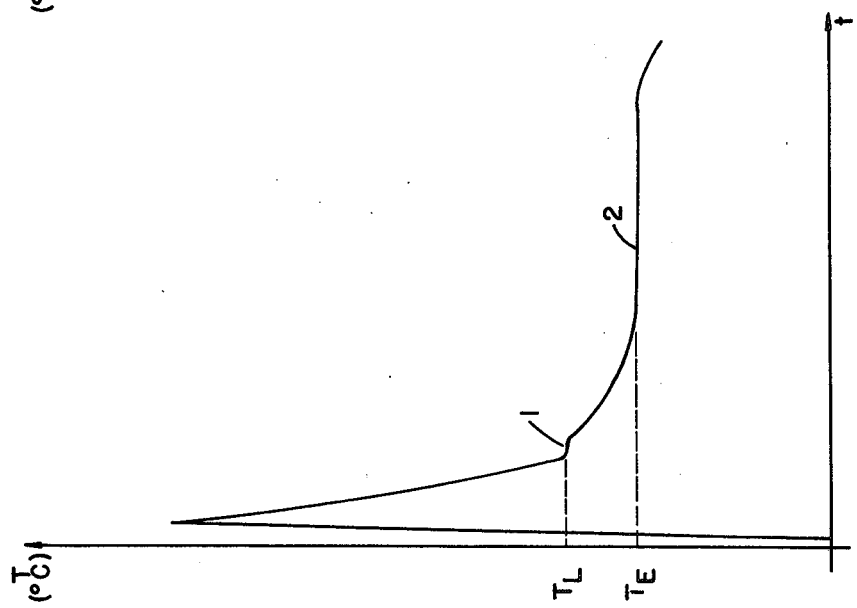
FIG. 1 shows a solidification curve of a nodular hypereutectic iron sample, obtained according to the invention.

FIG. 1 clearly shows the advantages of the method according to the invention when compared with FIG. 2. In this comparative example, two samples of the same nodular hypereutectic casting (composition: C:3.8%; Si:2.1%; P:0.04%) were studied. To the first sample 0.4% in weight of sulphur flour and 0.08% in weight of tellurium was added while only 0.08% in weight of tellurium was added to the second one.

In the curve of FIG. 1; one easily can see a first level 1 called "liquidus arrest," as well as a second level 2, called "solidus arrest," or "metastable eutectic arrest." Level 1 corresponds to the liquidus temperature ($T_L$), and level 2 corresponds to the eutectic temperature ($T_E$).

The knowledge of the temperatures ($T_L$ and $T_E$) corresponding to said two levels allows one to infer the carbon equivalent and the carbon content of the analysed iron sample using known methods of calculation.

In the example of FIG. 2, the temperatures corresponding to the liquidus and solidus arrests are totally indistinguishable due to undercooling phenomena peculiar to the gray solidification.

A sample solidifying according to the curve represented in FIG. 2 is also no use for certain analyses by means of an emission-spectrometer.

Figure 3:
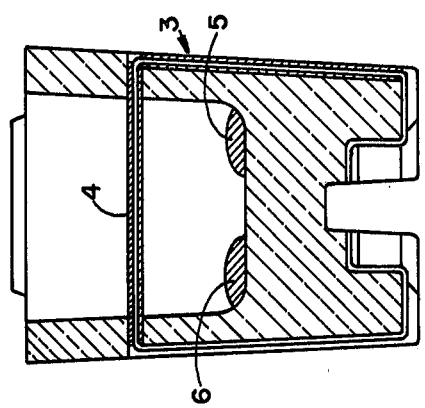
FIG. 3 represents a sampling crucible allowing the application of the method according to the invention.

The crucible used for the recording of the solidification curves in FIGS. 1 and 2 is represented in FIG. 3. It is of a well-known type, e.g. such as described in U.S. Pat. No. 3,946,594 and comprises a so-called crucible 3 of refractory equipped with a thermocouple 4 with low thermal inertia. A blob of tellurium 5, to which a suitable binder is added, adheres to the bottom of the crucible. Before recording FIG. 1, a second blob 6, containing sulphur, selenium or an oxide was also deposited on the bottom of the crucible. Crucible 3 has a capacity of about 300 g.

Although it is possible to mix the tellurium blob 5 with the second blob 6, it was found preferable to maintain the tellurium and the sulphur separated one from another in such a way as to obtain the certain fixation of magnesium and cerium before diffusion of tellurium.

The tellurium and the element capable of binding magnesium and cerium can also be disposed in the form of a wash, deposit of layers, but, for thermodynamical reasons, it is preferable to dispose of them in the form of blobs.

It is obvious that for analyses performed with the emission-spectrometer, the layers, blobs or deposits are previously disposed into a known device used for the sampling.

The present invention may be embodied in other specific forms without departing from the spirit or essential attributes thereof and, accordingly, reference should be made to the appended claims, rather than to the foregoing specification as indicating the scope of the invention.

I claim:

1. A method of promoting white solidification of an iron sample for analysis comprising:
   (a) obtaining a molten sample treated so as to solidify as cast iron selected from the group consisting of nodular and vermicular cast iron, said sample containing atoms selected from the group consisting of magnesium and cerium atoms which inhibit white solidification of said sample,
   (b) adding a material which will substantially bind said atoms in said sample, and
   (c) adding tellurium to said sample to effectively stabilize iron carbides formed during the cooling of said sample.

2. A method in accordance with claim 1 wherein said material is selected from the group consisting of sulphur and selenium.

3. A method in accordance with claim 1 wherein said material is sulphur added in an amount of 0.08% to 1% by weight.

4. A method in accordance with claim 1 wherein said material is selenium added in an amount of 0.2% to 0.3% by weight.

5. A method in accordance with claim 1 wherein said tellurium is added in an amount of about 0.1% by weight.

6. A method in accordance with claim 1 wherein said molten sample is poured into a refractory cup containing a temperature sensor therein.

7. A method in accordance with claim 6 wherein said material is sulphur and wherein said sulphur and said tellurium are introduced into said cup before said sample is poured into the cup.

8. A method in accordance with claim 6 wherein said molten sample is poured into said cup to a level above the level of said sensor and further comprising obtaining a cooling curve of said sample by recording the temperature of said sample as detected by said temperature sensor.

* * * * *